United States Patent [19]

Delis et al.

[11] Patent Number: 5,268,505
[45] Date of Patent: Dec. 7, 1993

[54] PREPARATION OF ADIPIC ACID BY HYDROCARBOXYLATION OF PENTENIC ACIDS

[75] Inventors: Philippe Delis, Saint-Didier-Au Mont-D'or; Philippe Denis, Decines; Jean-Michel Grosselin, Francheville; Francois Metz, Lyons, all of France

[73] Assignee: Rhone-Poulenc Chimie, Courbevoie, France

[21] Appl. No.: 811,584

[22] Filed: Dec. 20, 1991

[30] Foreign Application Priority Data

Dec. 20, 1990 [FR] France ............................... 90 16387

[51] Int. Cl.$^5$ ....................... C07C 51/10; C07C 51/14
[52] U.S. Cl. .................................................. 562/517
[58] Field of Search ........................................ 562/517

[56] References Cited

U.S. PATENT DOCUMENTS

| 3,579,551 | 5/1971 | Craddock et al. | 260/413 |
| 3,579,552 | 5/1991 | Craddock et al. | 260/413 |
| 4,788,333 | 11/1988 | Burke | 260/413 |
| 4,788,334 | 11/1988 | Burke | 562/522 |

FOREIGN PATENT DOCUMENTS 0274076 7/1988 European Pat. Off. .

Primary Examiner—Jose' G. Dees
Assistant Examiner—Joseph Conrad
Attorney, Agent, or Firm—Burns, Doane, Swecker & Mathis

[57] ABSTRACT

Adipic acid is prepared by hydrocarboxylating at least one pentenic acid in the presence of a catalytically effective amount of rhodium values, whether metallic rhodium or a compound thereof, and an iodine-containing promoter therefor, as well as in the presence of a cocatalytically effective amount of at least one of iridium, ruthenium, osmium or compound thereof.

13 Claims, No Drawings

PREPARATION OF ADIPIC ACID BY HYDROCARBOXYLATION OF PENTENIC ACIDS

BACKGROUND OF THE INVENTION

1. Field of the Invention

The present invention relates to the preparation of adipic acid by hydrocarboxylation of pentenic acids, and, more especially, to the preparation of adipic acid by reacting water and carbon monoxide with at least one pentenic acid.

2. Description of the Prior Art

European Patent Application No. 188,209 describes a process for the preparation of straight-chain dicarboxylic acids, in particular adipic acid, by reacting unsaturated monocarboxylic acids, notably pent-3-enoic acid, with carbon monoxide and water in the presence of a rhodium-based catalyst and an iodine-containing promoter, the reaction being carried out in a solvent such as methylene chloride at a temperature of 100° to 240° C. and under a total pressure of between 14 and 240 atm; a temperature ranging from 150° to 180° C. and a total pressure ranging from 24 to 40 atmospheres are considered to be preferred.

The selection of the solvent and the water content of the reaction mixture are critical according to this '209 application, such constraints, however, militating against the applicability of the process on an industrial scale.

U.S. Pat. No. 3,579,552 describes the use of a rhodium-based catalyst and an iodine-containing promoter in reactions for the hydrocarboxylation of olefins and certain of the derivatives thereof. However, the proportion of straight-chain acid produced remains insufficient.

U.S. Pat. No. 3,579,551 describes the use of an iridium-based catalyst and an iodine-containing promoter in reactions for the hydrocarboxylation of olefins and certain of the derivatives thereof. However, the activity of such a catalyst system remains inadequate.

Thus, serious need continues to exist for an improved catalyst system which simultaneously provides enhanced activity and enhanced selectivity for adipic acid while at the same time avoiding the above disadvantages and drawbacks to date characterizing the state of the art.

SUMMARY OF THE INVENTION

Accordingly, a major object of the present invention is the provision of an improved process for the preparation of adipic acid by hydrocarboxylation of at least one pentenoic acid in the presence of rhodium or of a rhodium compound and of an iodine-containing promoter, wherein the reaction is also carried out in the presence of at least one cocatalyst selected from among iridium, ruthenium, osmium and compounds thereof.

DETAILED DESCRIPTION OF THE PREFERRED EMBODIMENTS OF THE INVENTION

More particularly according to the present invention, by "pentenic acid" are intended pent-2-enoic acid, pent-3-enoic acid, pent-4-enoic acid and mixtures thereof.

Pent-4-enoic acid provides good results, but is not readily commercially available.

Pent-3-enoic acid, whether used alone or in admixture with its isomers, is more particularly appropriate, taking account of its availability and the satisfactory results which it provides.

The process according to the present invention requires the presence of a rhodium-based catalyst. Any source of rhodium values may be used.

Exemplary sources of rhodium which are suitable for carrying out the process of the invention include:

Rh metal; $Rh_2O_3$;
$RhCl_3$; $RhCl_3.3H_2O$;
$RhBr_3$; $RhBr_3.3H_2O$ ;
$RhI_3$; $Rh(NO_3)_3$; $Rh(NO_3)_3.2H_2O$;
$Rh_2(CO)_4Cl_2$; $Rh_2(CO)_4Br_2$; $Rh_2(CO)_4I_2$;
$Rh(CO)Cl[P(C_6H_5)_3]_2$;
$Rh[P(C_6H_5)_3]_2(CO)I$;
$Rh[P(C_6H_5)_3]_3Br$;
$Rh_4(CO)_{12}$; $Rh_6(CO)_{16}$; $Rh(CO)_2(acac)$;
$Rh(Cod)(acac)_2$; $Rh(acac)_3$;
$Rh_2(Cod)_2Cl_2.Rh_2(CO_2CH_3)_4$;
$HRh(CO)[P(C_6H_5)_3]_3$;
(Cod = 1,5-cyclooctadiene; acac = acetylacetonate).

The following are more particularly preferred for carrying out the process of the invention:
$Rh_2(Cod)_2Cl_2$;
$Rh_2(CO)_4Cl_2$;
$RhI_3$; $RhCl_3.3H_2O$; $Rh(acac)_3$;
$Rh(Cod)(acac)_2$; $Rh_2(CO_2CH_3)_4$; $Rh_4(CO)_{12}$; and $Rh_6(CO)_{16}$.

The amount of rhodium to be used may vary over wide limits.

In general, a catalytically effective amount, expressed in moles of rhodium metal per liter of reaction mixture, ranging from $10^{-3}$ to $10^{-1}$ provides satisfactory results. Smaller amounts may be used; however, it is observed that the rate of reaction is low. Higher amounts present disadvantages only in respect of the economics of the process.

Preferably, the rhodium concentration ranges from $5.10^{-3}$ to $10^{-2}$ mol/l, inclusive.

By the term "iodine-containing promoter" are intended HI and the iodine-containing organic precursor compounds capable of generating HI under the conditions of the reaction, and in particular $C_1$-$C_{10}$ alkyl iodides, with methyl iodide being more particularly preferred.

It will be appreciated that compounds such as $RhI_3$ may simultaneously constitute a useful source of rhodium as well as all or a fraction of the iodine-containing promoter.

The amount of iodine-containing promoter to be used is typically such that the molar ratio I/Rh is greater than or equal to 0.1. It is not desirable for this ratio to be higher than 20. Preferably, the molar ratio I/Rh ranges from 1 to 4, inclusive.

The presence of water is indispensable for carrying out the process according to the present invention. In general, the amount of water to be used is such that the molar ratio of water/pentenic acid(s) ranges from 1 to 10, inclusive.

A smaller amount presents the drawback of restricting the conversion. A larger amount is not desirable because of the loss in catalytic activity which is observed.

The process according to the present invention also requires the presence of at least one cocatalyst selected from among iridium, ruthenium, osmium and compounds thereof.

Exemplary sources of iridium which are suitable for carrying out the process of the invention Ir metal; $IrO_2$; $Ir_2O_3$;
$IrCl_3$; $IrCl_3.3H_2O$;
$IrBr_3$; $IrBr_3.3H_2O$;
$IrI_3$;
$Ir_2(CO)_4Cl_2$; $Ir_2(CO)_4I_2$;
$Ir_2(CO)_8$; $Ir_4(CO)_{12}$;
$Ir_2(CO)[P(C_6H_5)_3]_2 I$;
$Ir(CO)[P(C_6H_5)_3]_2 Cl$;
$Ir[P(C_6H_5)_3]_3I$;
$HIr[P(C_6H_5)_3]_3(CO)$;
$Ir(acac)(CO)_2$;
$[IrCl(Cod)]_2$
(Cod = 1,5-cyclooctadiene ; acac = acetylacetonate).

The following are examples of sources of ruthenium which are suitable for carrying out the process of the invention:

Ru metal; $RuO_2$; $RuO_4$;
$RuCl_3$; $RuCl_3.3H_3O$ ; $RuBr_3$; $RuI_3$;
$Ru(OAc)_3$; $RuCl_4$;
$Ru(CO)_5$; $Ru(CO)_{12}$; $[Ru(CO)_3Br_2]_2$;
$Ru(CO)_4I_2$; $Ru(acac)_3$; $RuCl(\eta-C_3H_5)$.

And the following are exemplary sources of osmium which are suitable for carrying out the process of the invention:

Os metal; OsO; $Os_2O_3$; $OsO_2$ : $OsOF_4$;
$OsCl_3$; $OsBr_3$; $OsCl_3.3H_2O$;
$OsCl_4$;
$Os_3(CO)_{12}$.

Among the sources of iridium, the following are more particularly preferred for carrying out the process of the invention:

$IrCl_3$; $IrCl(Cod)_2$; $Ir_4(CO)_{12}$

Among the sources of ruthenium, the following are more particularly preferred for carrying out the process of the invention:

$RuO_2.H_2 O$;
$RuCl_3.H_2O$ ; $RuCl_2(Cod)$ ; $Ru_3(CO)_{12}$; $Ru(acac)_3$.

And among the sources of osmium, the following are more particularly preferred for carrying out the process of the invention:

$OsCl_3$; $Os_3(CO)_{12}$.

The cocatalyst is advantageously selected from among iridium and the compounds thereof.

The molar ratio of the cocatalyst, expressed as metal M with respect to rhodium, may vary over wide limits, for example from 0.05 to 50, inclusive.

The M/Rh ratio preferably ranges from 0.1 to 5, inclusive.

The process according to the present invention is advantageously carried out in the liquid phase. It will of course be appreciated that the reaction mixture may contain a solvent or diluent. The following are exemplary solvents or diluents which are suitable according to the process of the invention: saturated aliphatic or aromatic carboxylic acids having up to 20 carbon atoms, and saturated aliphatic or aromatic hydrocarbons which are optionally chlorinated and are liquid under the conditions of reaction.

In a preferred embodiment of the invention, a saturated $C_1$–$C_6$ aliphatic carboxylic acid, preferably acetic acid, is used.

In another preferred embodiment of the invention, a chlorinated saturated aliphatic hydrocarbon is used, more preferably methylene chloride.

The amount of solvent or diluent, if such a solvent or diluent is indeed present in the reaction mixture, may be as high as 99% by volume of said mixture. To satisfactorily carry out the process of the invention, this amount will be greater than or equal to 10% and preferably range from 30% to 90% by volume, inclusive.

The reaction temperature typically ranges from 100° to 240° C. Advantageously, this temperature will range from 160° to 190° C., inclusive.

The reaction is carried out under a pressure higher than atmospheric pressure. The total pressure may vary over wide limits, for example from 2 to 150 bars. In general, good results are attained employing pressures ranging from 5 to 50 bars.

Substantially pure carbon monoxide or technical grade carbon monoxide, as is available commercially, may be used.

Upon completion of the reaction or of the time allotted thereto, the adipic acid is separated off by any appropriate means, for example by extraction and/or crystallization.

In order to further illustrate the present invention and the advantages thereof, the following specific examples are given, it being understood that same are intended only as illustrative and in nowise limitative.

EXAMPLE 1

0.1 mmol of rhodium in the form of $[RhCl(Cod)]_2$, 0.1 mmol of iridium in the form of $IrCl_3$, 20 mmol of pent-3-enoic acid, 35 mmol of water, 0.57 mmol of HI in the form of a 57% by weight aqueous solution thereof and 10 ml of acetic acid were introduced successively into a glass flask.

The flask was then placed in a stainless steel (HASTELLOY B2) autoclave of 125 cm³ capacity which had previously been purged with argon.

The autoclave was hermetically sealed, placed in an agitated furnace and connected to the compressed gas supply.

2 bars of CO were admitted cold into the autoclave and the autoclave was heated to 175° C. over the course of 25 minutes. The pressure in the autoclave was then 4 bars. It was adjusted to 10 bar.

After 30 minutes of reaction at temperature, the absorption of CO had ceased; the autoclave was then cooled and degassed.

The reaction mass was analyzed by gas phase chromatography and by high performance liquid chromatography.

The amounts of products formed (molar yield with respect to the pent-3-enoic acid charged) were as follows:

Valeric acid (Pa):  < 1%

Pent-2-enoic acid (P2):  = 6%

4-Methylbutyrolactone (M4L): 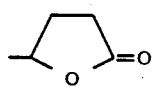 = 18%

Ethylsuccinic acid (A3): 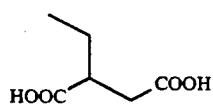 = 5.7%

Methylglutaric acid (A2): 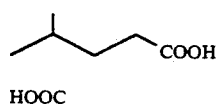 = 14.7%

Adipic acid (A1): 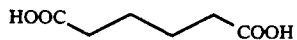 = 48%

The degree of linearity (L) was 76%
The degree of conversion of pent-3-enoic acid (DC) waw 100%.

EXAMPLES 2 AND 3; COMPARATIVE EXAMPLES (a) AND (b)

In the autoclave and repeating the procedure described for Example 1, a first series of experiments was carried out, modifying only the nature of the cocatalyst.

The particular conditions and the results obtained are reported in Table I below:

TABLE I

| Example | Cocatalyst | DC (%) | Yield (%) M4L | Yield (%) A1 | L (%) |
|---|---|---|---|---|---|
| 1 | IrCl$_3$ | 100 | 18 | 48 | 76 |
| 2 | RuCl$_3$ | 97 | 40 | 38 | 65 |
| 3 | OsCl$_3$ | 95 | 38 | 32 | 64 |
| a | — | 100 | 42 | 26 | 55 |
| b(*) | IRCl$_3$ | 83 | 86 | 1.2 | ε |

(*)experiment carried out in the absence of rhodium; reaction time 120 min.

EXAMPLES 4 to 8

In the autoclave and repeating the procedure described in Example 1, a second series of experiments was carried out on a batch containing different ruthenium compounds each time as cocatalyst, the nature of these compounds being reported in Table II below. The results reported in this Table were obtained under conditions which were otherwise identical and t in the Table represents the reaction time.

TABLE II

| Example | Catalyst | t min | DC (%) | Yield (%) M4L | Yield (%) A1 | L (%) |
|---|---|---|---|---|---|---|
| 4 | RuCl$_3$.H$_2$O | 60 | 89 | 23 | 45 | 66 |
| 5 | RuCl$_2$(Cod) | 300 | 93 | 29 | 44 | 70 |
| 6 | Ru(CO)$_{12}$ | 90 | 70 | 24 | 47 | 70 |
| 7 | Ru(acac)$_3$ | 60 | 67 | 25 | 42 | 66 |
| 8 | RuO$_2$.H$_2$O | 90 | 81 | 21 | 44 | 62 |

EXAMPLE 9

In the autoclave and repeating the procedure described for Example 1, an experiment was carried out on a batch containing 0.1 mmol of rhodium in the form of RhI$_3$, 0.1 mmol of iridium in the form of IrCl$_3$, 20 mmol of pent-3-enoic acid, 35 mmol of water and 10 mmol of acetic acid.

After 35 minutes of reaction at 175° C. under a total pressure of 10 bars, the results obtained were as follows:
DC(%)=100
A1(%)=64
M4L(%)=14
L(%)=86

EXAMPLES 10 to 17

A third series of experiments was carried out on a batch identical to that used in Example 9, modifying the reaction temperature (T) and/or the total pressure at temperature (P). The particular conditions and the results obtained are reported in Table III below:

TABLE III

| Example | T °C. | P (bar) | t (min) | DC % | Yield (%) M4L | Yield (%) A1 | L % |
|---|---|---|---|---|---|---|---|
| 10 | 175 | 5 | 45 | 100 | 10 | 67 | 82 |
| 11 | " | 8 | 35 | 100 | 9 | 67 | 81 |
| 9 | " | 10 | 35 | 100 | 14 | 64 | 86 |
| 12 | " | 25 | 30 | 100 | 10 | 63 | 76 |
| 13 | " | 47 | 30 | 99 | 10 | 66 | 80 |
| 14 | " | 100 | 60 | 83 | 10 | 53 | 65 |
| 15 | 190 | 15 | 30 | 100 | 10 | 65 | 78 |
| 16 | 160 | 10 | 65 | 99 | 9 | 65 | 79 |
| 17 | 140 | 10 | 105 | 59 | 6 | 48 | 58 |

EXAMPLE 18

The procedure of Example 9 was repeated, but replacing IrCl$_3$ by the same amount of [IrCl(Cod)]$_2$.

All other conditions being identical, substantially the same results were obtained.

EXAMPLE 19

The procedure of Example 9 was repeated, but replacing IrCl$_3$ by the same amount of Ir$_4$(CO)$_{12}$.

All other conditions being identical, substantially the same results were obtained.

EXAMPLE 20

The procedure of Example 9 was repeated, but replacing RhI$_3$ by an equivalent amount of [RhCl(Cod)]$_2$ and adding 0.3 mmol of HI to the batch.

All other conditions being identical, substantially the same results were obtained.

EXAMPLES 21 to 26; COMPARATIVE EXAMPLE (c)

A fourth series of experiments was carried out on a batch analogous to that used in Example 9, except that the amount of IrCl$_3$ and/or the nature of the pentenoic acid charged differed. The particular conditions and the results obtained at 175° C. under a total pressure of 10 bars are reported in Table IV below:

TABLE IV

| Example | Ir/Rh | Pentenic acid | t (min) | DC (%) | Yield (%) M4L | A1 | L (%) |
|---|---|---|---|---|---|---|---|
| 21 | 0.5 | pent-3-enoic | 90 | 100 | 17 | 58 | 76 |
| 22 | 1 | " | 60 | 100 | 12 | 62 | 83 |
| 23 | 2 | " | 50 | 100 | 17 | 54.5 | 85 |
| 24 | 5 | " | 50 | 100 | 39 | 28 | 90 |
| 25 | 1 | pent-4-enoic | 30 | 100 | 10 | 69 | 81 |
| 26 | 1 | pent-2-enoic | 75 | 92 | 12.5 | 50 | 82 |
| (c) | 0 | pent-2-enoic | 120 | 8 | 11 | 23 | 45 |

EXAMPLES 27 to 29

A fifth series of experiments was carried out on a batch analogous to that of Example 9, varying the concentration of water in the reaction mixture while maintaining the total volume (water + acetic acid) constant and equal to 12.5 ml.

The particular conditions and the results obtained are reported in Table V below:

TABLE V

| Example | H$_2$O (g/l) | t (min) | DC (%) | Yield (%) M4L | A1 | L (%) |
|---|---|---|---|---|---|---|
| 27 | 29 | 40 | 100 | 12 | 67 | 81 |
| 9 | 47 | 35 | 100 | 14 | 64 | 86 |
| 28 | 147 | 50 | 90 | 19 | 48 | 65 |
| 29 | 290 | 70 | 61 | 19 | 27 | 46 |

EXAMPLES 30 to 32

In the autoclave and repeating the procedure described for Example 1, a sixth series of experiments was carried out on a batch containing 0.1 mmol of iridium in the form of IrCl$_3$, 20 mmol of pent-3-enoic acid, 39 mmol of water, 10 ml of solvent, the precise nature of which is reported in Table VI below, and 0.1 mmol of rhodium in the form of [RhCl(Cod)]$_2$ (Examples 30 and 31) or in the form of RhI$_3$ (Example 32). In Examples 30 and 31 the batch also contained 0.3 mmol of HI. The results obtained at 175° C. and the particular conditions are reported in Table VI below:

TABLE VI

| Example | Nature of the solvent | P (bar) | t (min) | DC (%) | Yield (%) M4L | A1 | L % |
|---|---|---|---|---|---|---|---|
| 30 | Toluene | 10 | 60 | 70 | 6 | 21 | 75 |
| 31 | Methylene chloride | 30 | 60 | 81 | 6 | 50 | 75 |
| 32 | Valeric acid | 28 | 100 | 95 | 7 | 56 | 70 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of adipic acid, comprising hydrocarboxylating at least one pentenic acid in the presence of a catalytically effective amount of rhodium or compound thereof and an iodine-containing promoter therefor, and in the further presence of a cocatalytically effective amount of at least one of iridium, ruthenium, osmium or compound thereof.

2. The process as defined by claim 1, wherein the molar ratio of said cocatalyst, expressed as metal M, with respect to said rhodium values ranges from 0.05 to 50.

3. The process as defined by claim 1, said cocatalyst comprising iridium values or compound thereof.

4. The process as defined by claim 1, wherein the concentration of rhodium values ranges from $10^{-3}$ to $10^{-1}$ mol/l.

5. The process as defined by claim 1, wherein the I/Rh molar ratio is greater than or equal to 0.1 to 20.

6. The process as defined by claim 5, wherein the molar ratio of water/pentenic acid(s) ranges from 1 to 10.

7. The process as defined by claim 1, carried out in the presence of a saturated C$_1$-C$_6$ carboxylic acid.

8. The process as defined by claim 7, said saturated carboxylic acid comprising acetic acid.

9. The process as defined by claim 1, carried out in the presence of methylene chloride.

10. The process as defined by claim 1, wherein the M/Rh ratio ranges from 0.1 to 5.

11. The process as defined by claim 5, said I/Rh ratio ranging from 1 to 4.

12. The process as defined by claim 1, carried out at a temperature ranging from 100° to 240° C.

13. The process as defined by claim 12, carried out at a pressure ranging from 2 to 250 bar.

* * * * *